United States Patent [19]

Yamamoto

[11] Patent Number: 4,820,398
[45] Date of Patent: * Apr. 11, 1989

[54] ELECTROPHORESIS GEL SHEET

[75] Inventor: Shoichi Yamamoto, Saitama, Japan

[73] Assignee: Fuji Photo Film Co., Ltd., Kanagawa, Japan

[*] Notice: The portion of the term of this patent subsequent to Dec. 29, 2004 has been disclaimed.

[21] Appl. No.: 50,542

[22] Filed: May 14, 1987

[30] Foreign Application Priority Data

May 15, 1986 [JP] Japan ................... 61-111643

[51] Int. Cl.$^4$ .................. G01N 27/28; G01N 27/26
[52] U.S. Cl. ..................... 204/299 R; 204/182.8
[58] Field of Search ............... 204/299 R, 301, 182.8, 204/182.9, 180.1

[56] References Cited

U.S. PATENT DOCUMENTS 4,715,942 12/1987 Tezuka et al. .............. 204/182.8 X Primary Examiner—John F. Niebling
Assistant Examiner—John S. Starsiak, Jr.
Attorney, Agent, or Firm—Jules E. Goldberg

[57] ABSTRACT

An electrophoresis gel sheet is composed of electrically non-conductive organic polymer films, gel-casing spacers having predetermined thicknesses and disposed at both side edge portions between the two polymer films, and an electrophoresis medium of uniform thickness encapsulated between the two polymer films at the zone between the gel-casing spacers. A gap-forming spacer is secured to an outer surface of at least one of the polymer films constituting the electrophoresis gel sheet so that, when the electrophoresis gel sheet is inserted between electrically non-conductive supporting plates before electrophoresis, a gap is formed by the gap-forming spacer between a surface of the sheet supporting plate and the surface of the electrophoresis gel sheet which stand facing each other, whereby the surface of the sheet supporting plate and the surface of the electrophoresis gel sheet which stand facing each other are prevented from closely contacting each other, and the electrophoresis medium is prevented from being distorted by dust or the like.

4 Claims, 3 Drawing Sheets

ELECTROPHORESIS GEL SHEET

BACKGROUND OF THE INVENTION

1. Field of the Invention

This invention relates to an electrophoresis gel sheet used for carrying out electrophoresis of a substance having an electric charge in a solution, like protein or nucleic acid, in an electrophoresis apparatus used for separation, analysis or the like of the charged substance on the basis of the electric charge and the molecular weight thereof.

2. Description of the Prior Art

There has heretofore been known an operation of electrophoresis by which separation and analysis of charged molecules of protein, nucleic acid, their decomposition products, or the like, by utilizing migration of the charged molecules under the effect of an electric field are effected. For this purpose, various electrophoresis suporting media, for example, supporting media comprising polyacrylamide gel, agarose gel, or the like supported between the non-conductive plates or the polymer films, are used.

Particularly, in the biotechnology (genetic engineering) which has attracted attention in recent years, the electrophoresis operation is indispensable for determining a base sequence in the molecule of nucleic acid such as DNA fragment by utilizing autoradiography.

In the case where the operation of electrophoresis is carried out by use of the electrophoresis supporting medium (hereinafter referred to as a gel sheet) comprising two polymer films and polyacrylamide gel, agarose gel, or the like supported between the polymer films, the gel sheet is supported by being sandwiched between electrically non-conductive glass plates having predetermined thicknesses (not smaller than 3 mm) and loaded in this form into an electrophoresis apparatus in order to secure the gel sheet and to prevent exposure to an ionizing radiation emitted by diffused molecules migrating through the gel. At this time, if the gel sheet is supported between the glass plates with dust or the like intervening between the glass plates and the thin polymer films constituting the surfaces of the gel sheet, the gel portion where dust or the like is present is distorted together with the thin polymer films by the dust or the like, in the width direction and in the thickness direction, even though the dust or the like is very small and has a diameter of, for example, within the range of several microns to several tens of microns. Since the very small dust or the like clings to the surfaces of the polymer films constituting the gel sheet by electrostatic attraction given rise to on the surfaces of the polymer films, it is almost impossible to remove the clinging dust or the like completely. When the operation of electrophoresis is carried out with the gel being distorted by the dust or the like, it is difficult to obtain a normal pattern of migration bands, the migration pattern often being distorted. In the case where the operation includes the procedure of comparing multiple rows of the migration pattern in the width direction of the gel sheet as in the operation for determining the base sequence of DNA fragment, the distortion of the migration pattern results in low reliability of the information obtained on the base sequence in DNA fragment or the like. specifically, the migration speed of DNA fragment or the like under electrophoresis becomes uneven due to changes in the thickness of the gel membrane and the distortion of the gel while DNA fragment or the like passes through the gel portion where the thickness of the gel is uneven. As a result, the distortion of the migration pattern such as oblique bands or zigzag bands arise. If DNA fragment or the like under electrophoresis is once subjected to such a history, DNA fragment or the like continues to migrate in such distorted condition, even though the gel portion through which DNA fragment or the like passes thereafter is free from distortion.

SUMMARY OF THE INVENTION

The primary object of the present invention is to provide an electrophoresis gel sheet which is free from distortion of a migration pattern caused by distortion of gel and adversely affecting discrimination of a base sequence of DNA fragment or the like.

Another object of the present invention is to provide an electrophoresis gel sheet suitable for carrying out electrophoresis in a simple manner and with a low cost without giving rise to distortion of a migration pattern.

The present invention provides an electrophoresis gel sheet composed of two supporting members formed of an electrically non-conductive organic polymer film, gelcasing spacers having predetermined thicknesses and disposed at both side edge portions between the two organic polymer films, and an electrophoresis medium of uniform thickness encapsulated between the two organic polymer films at the zone between the gel-casing spacers, wherein the improvement comprises the provision of a gap-forming spacer secured to an outer surface of at least one of said organic polymer films constituting said electrophoresis gel sheet so that, when said electrophoresis gel sheet is inserted between electrically non-conductive supporting plates before electrophoresis, a gap is formed by said gap-forming spacer between a surface of said sheet supporting plate and the surface of said electrophoresis gel sheet which stand facing each other, whereby the surface of said sheet supporting plate and the surface of said electrophoresis gel sheet which stand facing each other are prevented from closely contacting each other, and the electrophoresis medium is prevented from being distorted by dust or the like.

With the electrophoresis gel sheet in accordance with the present invention, the gap-forming spacer is secured to at least one of the surfaces of the electrophoresis gel sheet which stand face to face with the sheet supporting plates formed of glass plates or the like. Therefore, even though dust or the like is present on the surfaces of the sheet supporting plates or the surfaces of the electrophoresis gel sheet when the electrophoresis gel sheet is inserted between the sheet supporting plates, the gap formed by the gap-forming spacer acts to prevent the gel membrane in the electrophoresis gel sheet from being compressed and distorted by the dust or the like. Accordingly, it becomes possible to obtain a normal migration pattern and to improve the accuracy of determination of the base sequence in DNA fragment or the like.

Also, since the gap-forming spacer is secured to the electrophoresis gel sheet, the physical strength of the electrophoresis gel sheet is increased by the gap-forming spacer, and it becomes possible to prevent the electrophoresis gel sheet from bending, thereby to eliminate expansion, compression or distortion of the gel and entry of bubbles into the gel, which are caused by bending of the electrophoresis gel sheet. Accordingly, processing of the electrophoresis gel sheet is facilitated.

Further, since the physical strength of the electrophoresis gel sheet is improved by the gap-forming spacer, the organic polymer film of less thickness for encapsulating the gel membrane may be used. This results in the decrease of the space between the gel membrane and an X-ray film in the course of exposure of the X-ray film to an ionizing radiation emitted by the substances in the gel membrane, and thus the shorter exposure time.

DESCRIPTION OF THE PREFERRED EMBODIMENTS

The present invention will hereinbelow be described in further detail with reference to the accompanying drawings.

Figure 1:
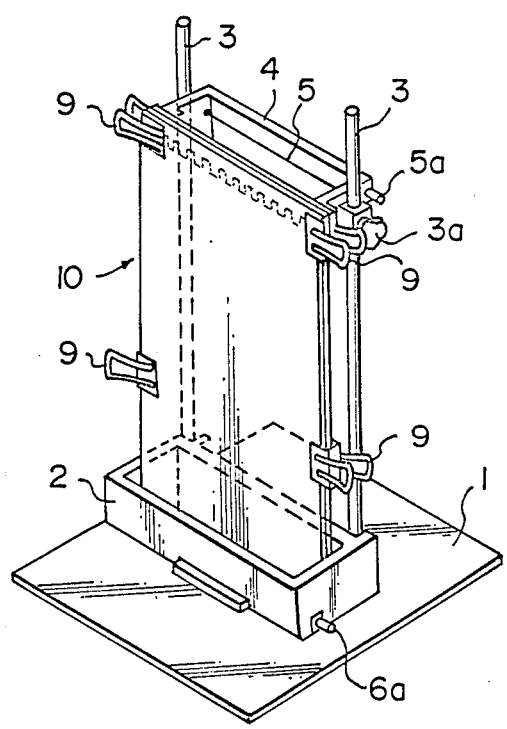
FIG. 1 is a perspective view showing an example of an electrophoresis apparatus wherein an embodiment of the electrophoresis gel sheet in accordance with the present invention is employed.

Referring to FIG. 1, an electrophoresis apparatus is basically composed of a supporting base 1, a lower buffer solution vessel 2, a pair of supporting rods 3, 3, an upper buffer solution vessel 4, and an electrophoresis sheet assembly 10. The lower buffer solution vessel 2 and the supporting rods 3, 3 are secured to the supporting base 1. The upper buffer solution vessel 4 is secured by set-screws 3a, 3a (only one set-screw is shown) to upper portions of the supporting rods 3, 3. Also, the electrophoresis sheet assembly 10 is mounted by use of clips 9, 9, 9, 9 such that an upper edge portion of the electrophoresis sheet assembly 10 is mounted on the upper buffer solution vessel 4 to stand facing a cutaway portion in the front surface of the upper buffer solution vessel 4, and a lower edge portion of the electrophoresis sheet assembly 10 enters the lower buffer solution vessel 2. An upper electrode 5 and a lower electrode 6 (the lower electrode 6 is not shown) constituted by a single platinum wire are respectively disposed in the upper buffer solution vessel 4 and the lower buffer solution vessel 2, and connected to external terminals 5a and 6a projecting outwardly from the side walls of the upper buffer solution vessel 4 and the lower buffer solution vessel 2. Therefore, electrophoresis can be carried out by introducing a buffer solution into the upper buffer solution vessel 4 and the lower buffer solution vessel 2 and applying a predetermined voltage across the external terminals 5a and 6a.

Figure 2:
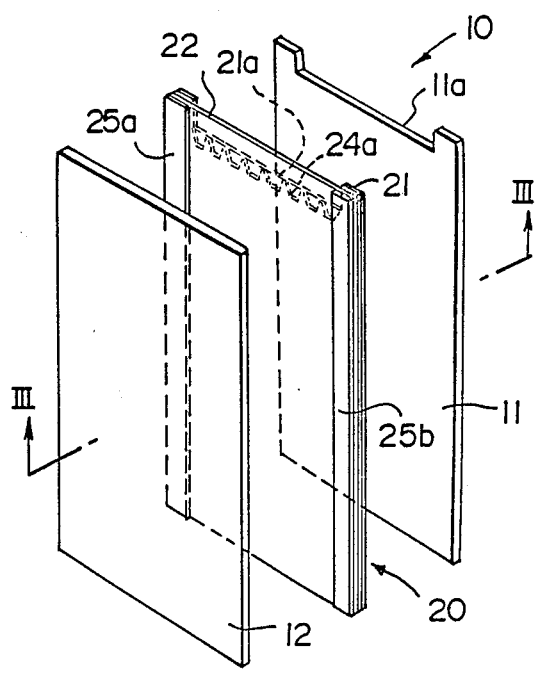
FIG. 2 is a perspective view showing the electrophoresis sheet assembly used in the apparatus of FIG. 1.
Figure 3:
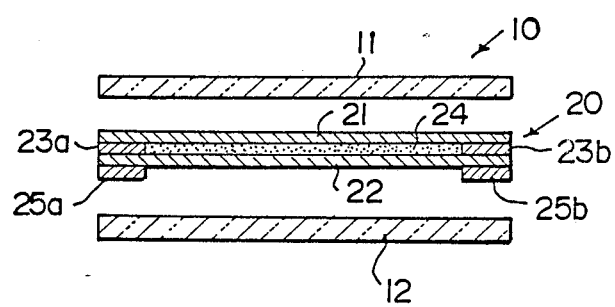
FIG. 3 is a sectional view taken along line III—III of FIG. 2, FIGS. 4 and 5 are perspective views showing further embodiments of the electrophoresis gel sheet in accordance with the present invention.

The configuration of the electrophoresis sheet assembly 10 will hereinbelow be described in detail. As shown in FIG. 2, the electrophoresis sheet assembly 10 is composed of a cutaway glass plate 11 having a cutaway portion 11a at an upper edge portion, a non-cutaway glass plate 12 without cutaway portion, and a gel sheet 20 inserted between the cutaway glass plate 11 and the non-cutaway glass plate 12. The cutaway glass plate 11 and the non-cutaway glass plate 12 act as supporting plates. Ceramic plates may be used in place of glass plates. As shown in FIG. 3, the gel sheet 20 is composed of sheet members 21 and 22 formed of an electrically non-conductive organic polymer film and disposed to stand facing each other, gel-casing spacers 23a and 23b having predetermined thicknesses and disposed at both side edge portions between the sheet members 21 and 22, and an electrophoresis gel membrane 24 having a thickness nearly equal to the thicknesses of the gel-casing spacers 23a and 23b and grasped between the sheet members 21 and 22. As shown in FIG. 2, the upper edge portion of the sheet member 21 facing the cutaway glass plate 11 is provided with a cutaway portion 21a having the same shape as the cutaway portion 11a formed at the upper edge portion of the cutaway glass plate 11, and a plurality of slots 24a, 24a, ... for introduction of a sample solution are formed at the upper edge portion of the gel membrane 24. Also, gap-forming spacers 25a and 25b formed of a polymer film or the like are secured to both side edge portions of the surface of the gel sheet 20 facing the non-cutaway glass plate 12. The gap-forming spacers 25a and 25b should preferably be formed of polyester, polyvinyl chloride or the like. Also, since the purpose of the gap-forming spacers 25a and 25b is to prevent the gel membrane 24 from being distorted by dust or the like which may be present between the gel sheet 20 and the non-cutaway glass plate 12, the thicknesses of the gap-forming spacers 25a and 25b should preferably be not smaller than 100 microns in view of the size of the dust or the like.

The electrophoresis sheet assembly 10 is constituted by inserting the gel sheet 20 between the cutaway glass plate 11 and the non-cutaway glass plate 12 by use of the clips 9, 9, 9, 9. When the electrophoresis sheet assembly 10 is inserted by grasping with the clips 9, 9, 9, 9, the upper edge portion of the electrophoresis sheet assembly 10 closely contacts the upper buffer solution vessel 4, and the buffer solution in the upper buffer solution vessel 4 contacts the upper edge portion of the gel membrane 24 via the cutaway portion 11a formed at the upper edge portion of the cutaway glass plate 11 and the cutaway portion 21a formed at the upper edge portion of the sheet member 21. On the other hand, since the gap-forming spacers 25a and 25b are secured to both side edge portions of the surface of the gel sheet 20 facing the non-cutaway glass plate 12, a gap of a predetermined thickness defined by the gap-forming spacers 25a and 25b is formed between the central portions of the non-cutaway glass plate 12 and the gel sheet 20. Therefore, even though dust or the like is present on the surfaces of the gel sheet 20 and the glass plates 11 and 12, there is no risk of the flexible gel sheet 20 being compressed by the dust or the like, and it is possible to prevent distortion of the gel membrane 24 in the gel sheet 20. In this case, the widths of the gap-forming spacers 25a and 25b should preferably be adjusted to be equal to the widths of the gel-casing spacers 23a and 23b secured to the gel sheet 20, and the gap-forming spacers 25a and 25b should preferably be aligned with the gel-casing spacers 23a and 23b so that the gel membrane 24 is not compressed by the gap-forming spacers 25a and 25b. An adhesive agent, a double-faced adhesive tape or the like may be used for securing the gap-forming spacers 25a and 25b to the sheet member 22.

In order to carry out electrophoresis by use of the electrophoresis apparatus constituted as mentioned above, the buffer solution is introduced into the upper buffer solution vessel 4 and the lower buffer solution vessel 2, and a predetermined sample solution is introduced into the slots 24a, 24a, ... at the upper edge portion of the gel membrane 24 of the gel sheet 20. Then, a predetermined voltage is applied across the external terminal 5a of the upper electrode 5 and the external terminal 6a of the lower electrode 6. The buffer solution in the upper buffer solution vessel 4 contacts the upper edge portion of the gel membrane 24 via the cutaway portion 11a of the cutaway glass plate 11 and the cutaway portion 21a formed in the sheet member 21 of the gel sheet 20. On the other hand, the lower edge portion of the electrophoresis sheet assembly 10 is projected into the lower buffer solution vessel 2, so that the lower edge portion of the gel membrane 24 contacts the buffer solution in the lower buffer solution vessel 2. Accordingly, the voltage applied across the external terminals 5a and 6a acts on the gel membrane 24 via the buffer solution, and electrophoresis of a sample solution introduced into the gel membrane 24 from its slots 24a, 24a, ... can be carried out.

Figure 4:
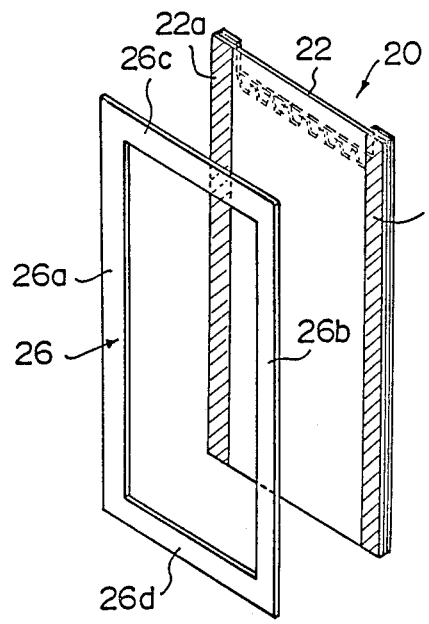
Figure 5:
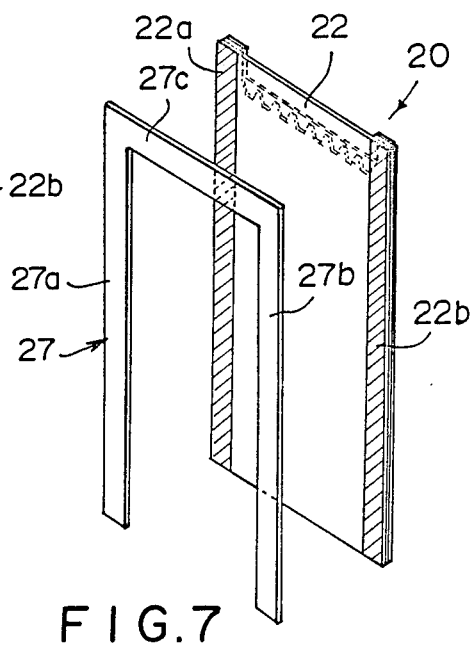

FIGS. 4 and 5 show further embodiments of the electrophoresis gel sheet in accordance with the present invention, which are different only in the shape of the gap-forming spacer from the gel sheet 20 shown in FIG. 2. In the embodiment of FIG. 4, a gap-forming spacer 26 is constituted by a rectangular frame-like sheet and has both side portions 26a and 26b adhered to both side edge portions 22a and 22b of the sheet member 22 which are indicated by hatching. An upper side portion 26c and a lower side portion 26d of the gap-forming spacer 26 are not adhered to the sheet member 22. On the other hand, the embodiment of FIG. 5 is provided with a gap-forming spacer 27 which is different from the gap-forming spacer 26 shown in FIG. 4 in that no lower side portion 26d is provided. Also in the embodiment of FIG. 5, both side portions 27a and 27b of the gap-forming spacer 27 are adhered to both side edge portions 22a and 22b of the sheet member 22 which are indicated by hatching, and an upper side portion 27c of the gap-forming spacer 27 is not adhered to the sheet member 22. In the case where the gap-forming spacer 26 or the gap-forming spacer 27 is used, the upper edge portion of the gel sheet 20 and the upper buffer solution vessel 4 are made to contact each other more closely by the upper side portion 26c of the gap-forming spacer 26 or the upper side portion 27c of the gap-forming spacer 27 when the gel sheet 20 is inserted between the cutaway glass plate 11 and the non-cutaway glass plate 12 and mounted on the apparatus.

Figure 6:
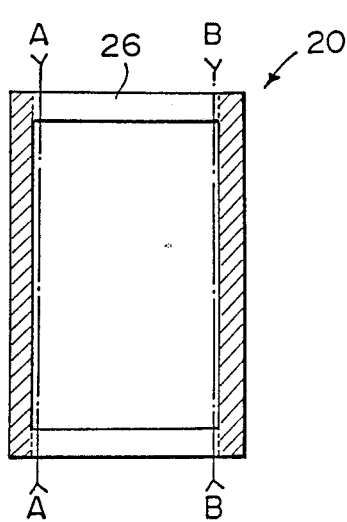
FIG. 6 is a front view showing the electrophoresis gel sheet of FIG. 4.

In the aforesaid embodiments, the gap-forming spacers 25a and 25b or the gap-forming spacer 26 or 27 is adhered to the sheet member 22 only at both side edge portions (22a and 22b in FIGS. 4 and 5). This is because the gel sheet 20 is to be cut off at positions slightly inward of both side edge portions (22a and 22b in FIGS. 4 and 5) after electrophoresis is finished. Specifically, as shown in FIG. 6 for the gel sheet 20 of FIG. 4 for example, the gel sheet 20 is cut along lines A—A and B—B after electrophoresis is finished, and the gap-forming spacer 26 (or the gap-forming spacers 25a and 25b in the embodiment of FIG. 2, or the gap-forming spacer 27 in the embodiment of FIG. 5) is separated from the gel sheet 20. Then, the sheet member 22 is closely contacted with an X-ray film so that the X-ray film is exposed to an ionizing radiation emitted by the radioactive substances in the gel membrane 24 in the migration pattern. In this case, in order to dispose the gel membrane 24 close to the X-ray film, the thickness of the sheet member 22 should preferably be as small as possible. When the gap-forming spacers 25a and 25b or the gap-forming spacer 26 or 27 is secured to the sheet member 22 as mentioned above, it becomes possible to obtain high rigidity of the sheet member 22, and therefore the sheet member 22 of less thickness may be used.

Figure 7:
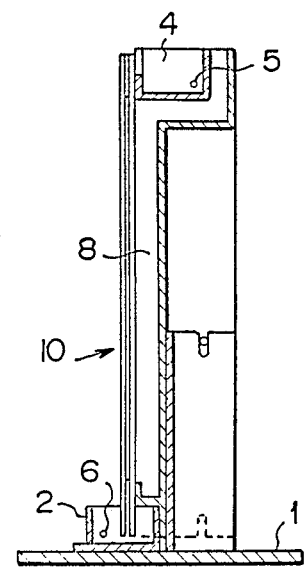
FIG. 7 is a sectional view showing another example of the electrophoresis apparatus.

In the aforesaid embodiments, the gap-forming spacers 25a and 25b or the gap-forming spacer 26 or 27 is secured to the surface of the sheet member 22 facing the noncutaway glass plate 12. However, the gap-forming spacers 25a and 25b or the gap-forming spacer 26 or 27 may be secured to the surface of the sheet member 21 facing the cutaway glass plate 11, or may be secured to both sheet members 21 and 22. On the other hand, as shown in FIG. 7, a temperature holding water vessel 8 having one side face constituted by the surface of the electrophoresis sheet assembly 10 on the side of the cutaway glass plate may be disposed between the upper buffer solution vessel 4 and the lower buffer solution vessel 2. In this case, the temperature of the electrophoresis sheet assembly 10 is made more uniform by water in the temperature holding water vessel 8, thereby to prevent generation of a smiling effect, i.e. the effect that, unless the temperature of the electrophoresis sheet assembly 10 is kept uniform, the temperature at both side edge portions of the gel membrane tends to be lower than at the central portion thereof, thus the migration speed of the charged substance at both side edge portions of the gel membrane differs from that at the central portion thereof, and consequently the migration pattern is bent in a circular arc form. In view of this, it is desired that the heat of water in the temperature holding water vessel 8 be well transmitted to the gel sheet 20 or vice versa, and therefore the gap-forming spacers 25a and 25b or the gapforming spacer 26 or 27 should preferably be secured to the surface of the sheet member 22 facing the non-cutaway glass plate 12.

I claim:

1. An electrophoresis gel sheet composed of two supporting members formed of an electrically non-conductive organic polymer film, gel-casing spacers having predetermined thicknesses and disposed at both side edge portions between the two organic polymer films, and an electrophoresis medium of uniform thickness encapsulated between the two organic polymer films at the zone between the gel-casing spacers, wherein the improvement comprises the provision of a gap-forming spacer secured to an outer surface of at least one of said organc polymer films constituting said electrophoresis gel sheet so that, when said electrophoresis gel sheet is inserted between electrically non-conductive supporting plates before electrophoresis, a gap is formed by said gap-forming spacer between a surface of said supporting plate and the surface of said electrophoresis gel sheet which stand facing each other, whereby the surface of said supporting plate and the surface of said electrophoresis gel sheet which stand facing each other are prevented from closely contacting each other.

2. An electrophoresis gel sheet as defined in claim 1 wherein said gap-forming spacer covers both side edge portions of said outer surface of at least one of said organic polymer films, and is secured to said outer surface by being adhered at both side edge portions of said outer surface.

3. An electrophoresis gel sheet as defined in claim 1 wherein said gap-forming spacer covers both side edge portions and upper and lower edge portions of said outer surface of at least one of said organic polymer films, and is secured to said outer surface by being adhered only at both side edge portions of said outer surface.

4. An electrophoresis gel sheet as defined in claim 1 wherein said gap-forming spacer covers both side edge portions and an upper edge portion of said outer surface of at least one of said organic polymer films, and is secured to said outer surface by being adhered only at both side edge portions of said outer surface.

* * * * *